United States Patent
Deck

(10) Patent No.: US 8,679,132 B2
(45) Date of Patent: Mar. 25, 2014

(54) INSERTION SYSTEM

(75) Inventor: Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 246 days.

(21) Appl. No.: 13/171,001

(22) Filed: Jun. 28, 2011

(65) Prior Publication Data

US 2012/0010482 A1    Jan. 12, 2012

(30) Foreign Application Priority Data

Jul. 10, 2010    (EP) .................................... 10007140

(51) Int. Cl.
*A61B 19/00* (2006.01)
(52) U.S. Cl.
USPC .......................................... 606/129; 606/181
(58) Field of Classification Search
USPC ......... 600/116, 417, 429, 562, 564, 565, 566, 600/567, 568, 583; 604/136, 137, 138, 139; 606/117, 181, 182, 183, 129
See application file for complete search history.

(56) References Cited

U.S. PATENT DOCUMENTS

| | | | |
|---|---|---|---|
| 4,899,756 A * | 2/1990 | Sonek | 600/461 |
| 7,842,060 B2 | 11/2010 | List | |
| 2002/0128570 A1 * | 9/2002 | Bowman et al. | 600/567 |
| 2002/0156376 A1 | 10/2002 | Wang et al. | |
| 2008/0140009 A1 | 6/2008 | Haueter et al. | |
| 2009/0192469 A1 | 7/2009 | Bognar | |
| 2010/0168618 A1 | 7/2010 | List | |

FOREIGN PATENT DOCUMENTS

| | | |
|---|---|---|
| WO | WO 89/11820 | 12/1989 |
| WO | WO 2008/133702 | 11/2008 |
| WO | WO 2009/024521 | 2/2009 |
| WO | WO 2009/047512 | 4/2009 |
| WO | WO 2010/040448 | 4/2010 |

\* cited by examiner

*Primary Examiner* — Ryan Severson
*Assistant Examiner* — Jonathan W Miles
(74) *Attorney, Agent, or Firm* — Harness, Dickey

(57) ABSTRACT

An insertion system for inserting a sensor into fatty tissue, comprising an insertion device and an insertion needle containing a sensor, wherein the insertion device comprises a holder for the insertion needle, and a piercing mechanism so as to move the holder, with the needle held by the same, in a feed direction for a puncture. The piercing mechanism changes the feed direction during the puncture so that, at the end of the puncture, an insertion needle held by the holder is oriented obliquely or perpendicular to the initial feed direction. Also provided are methods for controlling a needle moved by an insertion device.

10 Claims, 2 Drawing Sheets

INSERTION SYSTEM

CROSS-REFERENCE TO RELATED APPLICATIONS

This application claims the benefit and priority of European Patent Application No. 10 007 140.6, filed Jul. 10, 2010. The entire disclosure of the above application is incorporated herein by reference.

BACKGROUND

The invention relates to an insertion system for inserting a sensor into a fatty tissue.

Insertion systems for inserting a sensor or a cannula into fatty tissue are described in WO 2010/040448 A1, Deck et al., published Apr. 15, 2010. A system for inserting a sensor into the fetal scalp is described in WO 89/11820, Band et al., published Dec. 14, 1989. In this system, a semi-circularly curved insertion needle is introduced into the skin using a rotational movement, so that the needle tip—similar to a surgical suture—generates an entry opening in the skin at the beginning of the piercing movement and an exit opening in the skin at the end of the piercing movement, through which the needle tip exits.

SUMMARY

Sensors for measuring analyte concentrations in vivo, for example the glucose concentration, are inserted into a patient's subcutaneous fatty tissue by introducing a needle into the fatty tissue. Insertion needles that are customary for this purpose generally are designed as hollow needles or V-shaped channels, in which a sensor is located, for example an electrode system for electrochemical measurements. Following the puncture, the insertion needle is pulled out of the body tissue, with the sensor remaining in the puncture wound that is generated.

In a similar fashion, cannulas are inserted into fatty tissue, for example for infusing insulin or other active medical substances.

Insertion apparatuses are frequently composed of a base unit, which is glued onto a patient's body, and a piercing device, which is coupled to the base unit for an insertion and subsequently is removed. In addition, insertion apparatuses are known that consist only of a piercing device.

Insertion systems are frequently operated directly by patients, for example to insert sensors for measuring the glucose concentration. It is therefore a constant goal in the development of insertion systems to ensure that these can be operated as easily and safely as possible, that they reliably anchor sensors in the fatty tissue and enable precise measurements. In addition, the pain that is associated with the puncture of an insertion needle should be substantially minimized to the extent possible.

This object is achieved by an insertion system having the characteristics described herein by a method for controlling the piercing movement of a needle described herein.

During a puncture, the piercing mechanism of an insertion system according to the invention first moves the holder of the insertion needle linearly in a first feed direction and then changes the feed direction during the puncture, so that the insertion needle is oriented obliquely or perpendicularly to the first feed direction at the end of the puncture. In this way, the following advantages can be achieved:

The insertion needle can impinge on the skin surface at a steep angle or even perpendicularly. The steeper the impingement angle, the better can the insertion needle penetrate into fatty tissue beneath the skin without pain. A flat impingement angle is associated with the risk that the skin surface gives way to the impinging needle and is displaced, which causes additional pain.

After penetrating the skin surface, the insertion needle can be pushed with a changed feed direction obliquely into the subcutaneous fatty tissue using an insertion system according to the invention. In this way it is possible for the sensor to be surrounded over a large length by fatty tissue, despite a small penetration depth of the insertion needle. A reduced penetration depth advantageously decreases the risk of injuring muscles located beneath the fatty tissue and increases the length of the sensor available for measurements.

The invention is particularly suited for inserting sensors for measuring analyte concentrations, for example the concentration of glucose, cholesterol or lactate.

According to the invention, at the end of the piercing movement the insertion needle points in a direction that is oblique or perpendicular to the direction in which the insertion needle points at the beginning of the piercing movement. The insertion needle is preferably straight. However, a curved insertion needle can be employed as well. Regardless of the shape, an insertion needle is oriented in the direction in which the tip thereof points.

A piercing movement according to the invention can be generated, for example, in that the insertion needle holder of the insertion device carries out a movement containing a curve during a puncture. A curve can change the feed direction of the insertion needle, so that the insertion needle, at the end of the puncture, is oriented obliquely or perpendicularly to the orientation thereof at the beginning of the puncture. However, change in the feed direction of the insertion needle can also be achieved subsequent to a first movement phase, for example, by a linear movement of the insertion needle holder transversely or obliquely to the original orientation of the insertion needle, which is to say, the orientation at the beginning of the piercing movement. The orientation of the insertion needle at the beginning of the piercing movement preferably agrees with the feed direction at the beginning of the piercing movement.

A piercing movement according to the invention can be achieved particularly advantageously in that the insertion needle holder, during a puncture, performs a movement that during a starting phase is a linear feed movement in a first feed direction, and that during an end phase is a linear feed movement in a second feed direction, which is oriented obliquely or perpendicularly to the first feed direction. Between these two linear movement sections of the insertion needle holder, a curved movement of the insertion needle holder or a transverse movement of the insertion needle holder can be carried out, for example, so as to change the feed direction.

The insertion needle holder can be stopped prior to changing the feed direction. However, a simple movement control with the desired change in the feed direction can also be achieved by only decelerating the insertion needle holder after a first linear movement phase, followed by further movement phases without stopping. In general, however, it is also possible that the speed of the insertion needle holder does not change during the change in the feed movement.

According to an advantageous refinement of the invention, the piercing mechanism pulls the holder back after a first feed movement by a portion of the distance traveled during the first feed movement and later causes a second feed movement. The skin can first be depressed by an impinging insertion needle before the insertion needle penetrates the skin. It is therefore generally advantageous to select the length of the first feed movement slightly larger than would be required for piercing the skin under ideal conditions. After the first feed movement, the needle can then be pulled back slightly in the fatty tissue and later the second feed movement can follow. For example, the tip of the insertion needle can be pushed out of the insertion device with the first feed movement, wherein a subsequent pull-back movement ends before the tip of the insertion needle enters the interior of the insertion device again.

The orientation of the insertion needle at the end of the puncture preferably deviates by at least 20°, particularly preferred by at least 40°, and most particularly preferred by at least 70° from the orientation of the insertion needle at the beginning of the puncture, and thus from the initial feed direction. In general, the advantage of a larger usable sensor length, with a low-pain puncture and lower risk of injury to deeper muscle tissue, can be utilized to an even greater extent the less the orientation of the insertion needle during impingement on the skin surface deviates from a perpendicular with respect to the skin surface, and the more the orientation of the insertion needle deviates from the perpendicular at the end of the piercing movement. From a medical perspective, a perpendicular impingement of the insertion needle on the skin and a horizontal orientation of the sensor beneath the skin are therefore optimal. However, the control of the movement of the insertion needle generally becomes the more complex the more the feed direction is to be changed during a puncture. Suitable movement control can be achieved, for example, by a piercing mechanism having a control with a cam and a cam follower. A further possibility is a mechanical linkage, for example a four-bar mechanism.

In a method according to the invention for controlling the piercing movement of a needle moved by an insertion apparatus, at the beginning of the piercing movement, the needle is moved linearly in a feed direction that agrees with the longitudinal direction of the needle. The special characteristic according to the invention is that during the puncture the feed direction of the needle is changed, so that at the end of the puncture the needle is oriented obliquely or perpendicularly to the initial feed direction. The orientations of the needle at the beginning of the piercing movement and at the end of the piercing movement are therefore oblique or perpendicular in relation to each other.

After a first feed movement, the needle is preferably pulled back by a portion of the advancement that was caused, and later, during a further feed movement, it is pushed obliquely or perpendicularly to the direction of the first feed movement. The pull-back movement can also be a linear movement, like the first feed movement.

Suitable control of movement can be achieved, for example, by means of a cam and cam follower. The cam has a first, rectilinear section for the first feed movement. A second section, which is used to change the feed direction, adjoins the first section. The second section is preferably curved; however, it can also be rectilinear, oblique or perpendicular to the first section. The second section can adjoin the end of the first section. To cause a pull-back movement, however, the second section of the cam may also start between the beginning and end of the first section. A cam follower then first moves from the beginning of the first section to the end of the first section and moves past the beginning of the second section. Thereafter, a portion of the first section is traveled in the reverse direction until the beginning of the second section is reached. Preferably a third section adjoins the second section of the cam, the third section causing a second feed movement. The third section preferably is rectilinear.

The described method for controlling the piercing movement of a needle moved by an insertion apparatus can advantageously be used to achieve that the needle impinges on the skin at a steep angle, or even perpendicularly, and that the feed direction of the needle is changed after the skin is penetrated, so that a sensor is surrounded by fatty tissue over a large length, despite a small penetration depth. An accordingly equipped insertion apparatus carries out the method according to the invention for controlling the piercing movement by nature as soon as a puncture is triggered, even if the insertion apparatus has not been placed on the skin of a patient, so that the needle then is not introduced in the patient.

DRAWINGS

Further details and advantages of the invention will be described based on an embodiment with reference to the attached drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
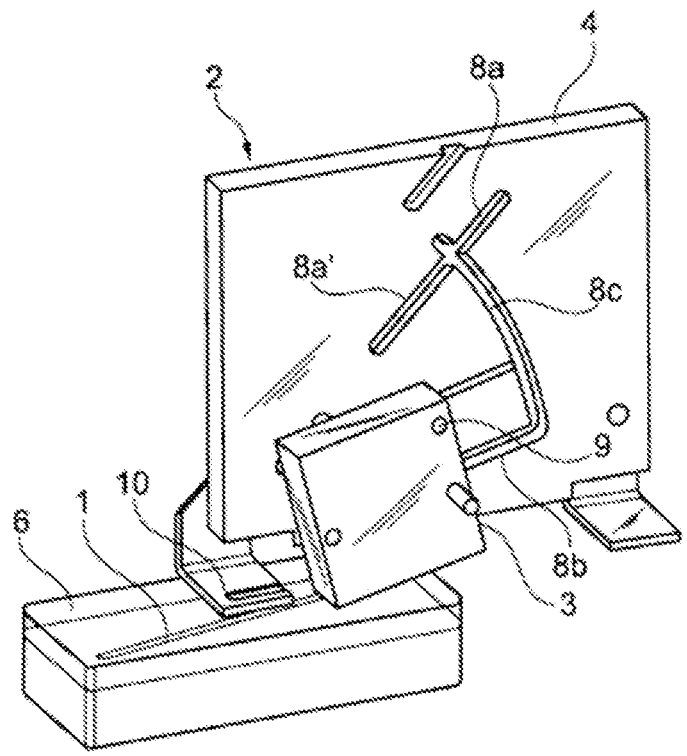
FIG. 1 is a schematic illustration of an insertion system.

FIG. 1 is a schematic illustration of an insertion system for inserting a sensor in fatty tissue of the stomach. The insertion system comprises an insertion needle 1 containing a sensor 11 (FIG. 3), and an insertion device 2. FIG. 1 shows the insertion device 2 without housing, control elements and similar parts, which are not required for understanding of the piercing movement and the related movement control.

The insertion device 2 has a holder 3 for the rectilinear insertion needle 1 and a piercing mechanism 4 to move the holder 3, together with a needle 1 held by the same, for a puncture. The piercing mechanism can comprise an electric drive or, for example, convert muscle power applied by a user into a piercing movement, as is known from WO 2010/040448 A1, Deck et al., published Apr. 15, 2010, or DE 10 2004 059 491 A1, List, published Jul. 6, 2006, for example.

Figure 3:
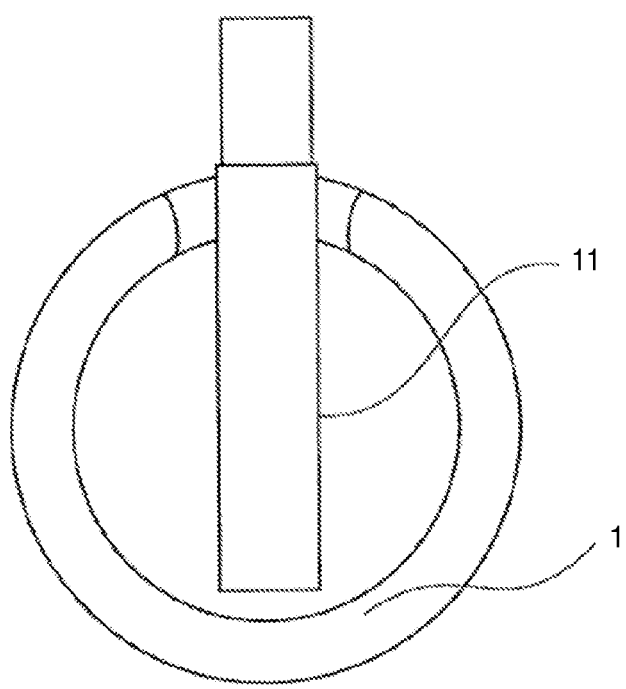
FIG. 3 is an illustration of a slotted cannula insertion needle with a sensor.

FIG. 3 is an illustration of an insertion needle 1 with a sensor 11. As shown, the insertion needle 1 can, for example, simply be a slotted cannula, which is held directly by the holder 3 of the insertion device. It is also possible for the insertion needle to comprise a plastic body in which a cannula is seated. In such a case, it is sufficient for the holder 3 of the insertion device to hold the plastic body of the insertion needle. In general terms, the holder 3 of the insertion device can hold the insertion needle 1 directly or indirectly.

Figure 2:
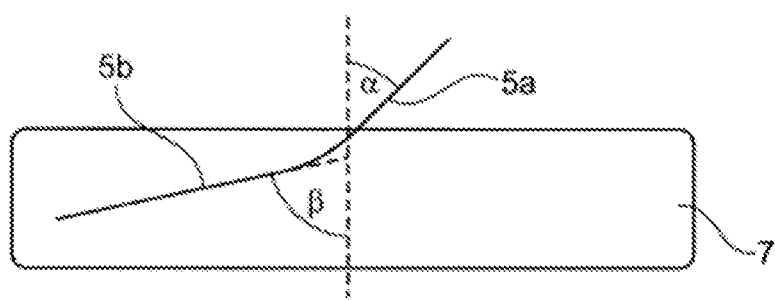
FIG. 2 is a schematic illustration of a movement path of an insertion needle.

During a puncture, the piercing mechanism 4 of the insertion system shown schematically in FIG. 1 causes the movement path 5a, 5b shown in FIG. 2. FIG. 2 is a schematic illustration of the path of the tip of an insertion needle 1 during impingement on a skin surface 6 and subsequently in the fatty tissue 7 located underneath. The movement path contains a rectilinear starting section 5a and a rectilinear ending section 5b, which runs obliquely to the starting section 5a.

FIG. 2 also shows that during a puncture the piercing mechanism of the insertion device shown schematically in FIG. 1 first moves the holder, and thereby also an insertion needle held by the same, in a first feed direction and then, during the puncture, changes the feed direction, so that an insertion needle held by the holder is oriented obliquely with respect to the first feed direction at the end of the puncture. The movement performed by the holder, and thus by the insertion needle, during a puncture is a linear movement in the first feed direction in a first movement section 5a, and in a further movement section 5b it is a linear movement in a second feed direction, which is oriented obliquely with respect to the first feed direction. The holder 3 performs a curved movement in the embodiment shown between the two linear movement sections 5a, 5b.

Upon impinging on the skin surface 6 of a patient, the insertion needle 1 thus forms a first angle α with a line perpendicular to the skin surface. After penetrating the skin, the piercing mechanism changes the feed direction of the insertion needle, so that at the end of the piercing movement the insertion needle 1 forms a second angle β with the perpendicular in relation to the skin surface that is greater than the first angle α. Steep impingement prevents a lateral displacement of the skin 6 around the puncture point, while the second linear movement section ensures good anchoring of the sensor 11 in the fatty tissue. In the movement path shown in FIG. 2, the length of the sensor 11 can be selected arbitrarily. The first angle α preferably ranges between 0° and 45°. The second angle β preferably ranges between 45° and 90°. The orientation of the insertion needle 1 at the end of the puncture deviates in the embodiment shown by more than 30° from the orientation of the insertion needle 1 at the beginning of the puncture.

In the shown embodiment, the movement path shown in FIG. 2 is generated by means of a slotted control member, which is to say a cam, on which a cam follower 9 travels, for example a pin connected to the holder 3.

The control in the embodiment shown has a cam comprising two linear sections 8a, 8b, which are oblique in relation to each other and connected by a curved section 8c. Each of the two linear sections 8a, 8b of the cam causes a linear movement section of the piercing movement. The curved section of the cam 8c causes a change in the feed direction, so that the second linear movement section 5b runs obliquely with respect to the first linear movement section 5a.

In the embodiment shown, the insertion needle 1 can be pulled back slightly after a first linear movement section 5a before the orientation of the needle is changed by the cam section 8c. The curved cam section 8c therefore does not adjoin the end of the linear cam section 8a. The cam section 8a' shown in FIG. 1 can be used for a feed movement, and subsequent return movement, of the needle 1. In the embodiment shown, the needle carries out a pivot movement to change the orientation, while the needle tip protrudes from the insertion device and is thus located in the fatty tissue.

The insertion device shown schematically in FIG. 1 comprises an exit opening 10 for the insertion needle 1 at the bottom side. The exit opening 10 is a slot in the embodiment shown. By changing the feed direction of the insertion needle through a pivot movement, as is the case in the shown embodiment, the necessary mobility of the insertion needle 1 after piercing the skin surface can be achieved and the skin surface can advantageously be fixed to facilitate penetration.

The piercing mechanism changes the feed direction of the insertion needle after the tip of the insertion needle 1 has exited the exit opening 10 of the piercing device, which is to say after the skin surface 6 has been penetrated. The feed direction of the insertion needle 1 can also be changed slightly before impingement on the skin surface. However, the piercing mechanism preferably does not change the feed direction of the insertion needle until after the tip of the insertion needle 1 has exited the exit opening 10 of the piercing device. To be able to use the advantages of a change in the feed direction, the change in the feed direction after penetrating the skin 6 is important. While changes in the feed direction prior to penetrating the skin 6 are not harmful, they offer no advantage and generally only make the control more complicated.

The edge of the exit opening 10 defines an area. When the tip of the insertion needle 1 exits the exit opening 10, the insertion needle forms the first angle α with a perpendicular in relation to this area. The perpendicular in relation to the area defined by the edge of the exit opening 10 agrees during a puncture with the perpendicular in relation to the skin surface. After the needle tip exits the opening 10, the piercing mechanism changes the feed direction of the insertion needle 1, so that at the end of the piercing movement the insertion needle 1 forms the second angle β with the perpendicular in relation to the surface defined by the edge of the exit opening 10.

| Reference numerals | |
|---|---|
| 1 | Insertion needle |
| 2 | Insertion device |
| 3 | Holder |
| 4 | Piercing mechanism |
| 5a | Starting section of the movement path |
| 5b | Ending section of the movement path |
| 6 | Skin surface |
| 7 | Fatty tissue |
| 8a | Cam section |
| 8b | Cam section |
| 8c | Cam section |
| 9 | Cam follower |
| 10 | Exit opening |
| α | First angle |
| β | Second angle |

What is claimed is:

1. An insertion system for inserting a sensor or a cannula into fatty tissue, comprising
   an insertion device and an insertion needle containing a sensor or a cannula,
   the insertion device having a holder for the insertion needle and a piercing mechanism so as to move the holder, together with a needle held by the holder, for a puncture linearly in a feed direction,
   characterized in that during the puncture the piercing mechanism changes the feed direction of the insertion needle after a tip of the insertion needle has exited an exit opening of the insertion device, and the piercing mechanism does not change the feed direction until after the tip of the insertion needle has exited the exit opening so that, at the end of the puncture, the insertion needle held by the holder is oriented obliquely or perpendicular to an initial feed direction.

2. The insertion system according to claim 1, characterized in that during a puncture the holder carries out a movement that contains a curve.

3. The insertion system according to claim 1, characterized in that during a puncture the holder carries out a movement that contains a movement section with a linear feed movement in a first feed direction and a later movement section with a linear movement in a second feed direction, which is oriented obliquely or perpendicularly to the first feed direction.

4. The insertion system according to claim 1, characterized in that the piercing mechanism pulls the holder back after a first feed movement and later causes a second feed movement.

5. The insertion system according to claim 1, characterized in that the piercing mechanism contains a cam control.

6. The insertion system according to claim 1, characterized in that, when the tip exits the exit opening, the insertion needle forms a first angle with a perpendicular in relation to an area defined by the edge of the opening, and the piercing mechanism then changes the feed direction of the insertion needle so that, at the end of a piercing movement, the insertion needle forms a second angle with the perpendicular, the second angle being greater than the first angle.

7. The insertion system according to claim 1, characterized in that the exit opening is a slot.

8. The insertion system according to claim 1, characterized in that, upon impingement on a skin surface of a patient, the insertion needle forms a first angle with a perpendicular in relation to a skin surface, and after the skin has been penetrated, the piercing mechanism changes the feed direction of the insertion needle so that, at the end of a piercing movement, the insertion needle forms a second angle with the perpendicular in relation to the skin surface, the second angle being greater than the first angle.

9. The insertion system according to claim 8, characterized in that the first angle is 0° to 45° and the second angle is 45° to 90°.

10. The insertion system according to claim 1, characterized in that the orientation of the insertion needle at the end of a puncture deviates from the orientation of the insertion needle at the beginning of a puncture by at least 20°.

* * * * *